United States Patent [19]

Yamasaki et al.

[11] Patent Number: 4,666,975

[45] Date of Patent: May 19, 1987

[54] ABSORPTIVE MATERIAL

[75] Inventors: Harumasa Yamasaki; Takatoshi Kobayashi, both of Wakayama; Osamu Ito; Akira Sakurai, both of Utsunomiya; Yuzo Sumida, Wakayama, all of Japan

[73] Assignee: Kao Corporation, Tokyo, Japan

[21] Appl. No.: 707,718

[22] Filed: Mar. 4, 1985

[30] Foreign Application Priority Data

| Mar. 5, 1984 | [JP] | Japan | 59-41725 |
| Mar. 5, 1984 | [JP] | Japan | 59-41726 |
| Mar. 5, 1984 | [JP] | Japan | 59-41727 |
| Mar. 5, 1984 | [JP] | Japan | 59-41728 |
| Mar. 5, 1984 | [JP] | Japan | 59-41729 |

[51] Int. Cl.⁴ ............ C08F 2/32; C08G 59/42
[52] U.S. Cl. .................... 524/733; 525/119; 525/154; 525/382; 525/384; 525/385
[58] Field of Search ........ 527/300; 524/733; 525/119, 154, 382, 385, 384

[56] References Cited

U.S. PATENT DOCUMENTS

| 4,093,776 | 6/1978 | Aoki et al. | 526/207 |
| 4,340,706 | 7/1982 | Obayashi et al. | 526/311 |
| 4,446,261 | 5/1984 | Yamasaki et al. | 524/733 |

FOREIGN PATENT DOCUMENTS 158210 of 1982 Japan.
2104904 3/1983 United Kingdom.

Primary Examiner—John Kight
Assistant Examiner—Nathan M. Nutter
Attorney, Agent, or Firm—Flynn, Thiel, Boutell & Tanis

[57] ABSTRACT

A polymer in the form of particles is water-insoluble and water-sellable, containing carboxyl or carboxylate groups. It has a physiological saline absorption quantity of 40 to 90 grams per one gram of the polymer, a physiological saline absorption rate of at least 8 ml per 0.3 gram of the polymer, a gel strength of 33 to 200 g/cm2 when it has been swollen to saturation with ion-exchange water. It is useful as an absorbent in a sanitary article.

5 Claims, 2 Drawing Figures 0.3g OF SAMPLE
GLASS FILTER OF 70mm DIAMETER
THE SAME LEVEL OF WATER BEFORE WATER ABSORPTION
20 MINS. AFTER WATER ABSORPTION
PHYSIOLOGICAL SALINE WEIGHT
SMOOTH SURFACE PLATE OF 60 mm DIAMETER
SWOLLEN POLYMER

ABSORPTIVE MATERIAL

The present invention relates to an absorptive material which comprises a water-insoluble, water-swellable high-molecular material containing carboxyl or carboxylate groups and having remarkably improved liquid absorption characteristics and excellent gel strength. More particularly, the present invention relates to an absorptive material suitable for use as sanitary napkin, disposable diaper, humor absorption pad for medical use, etc.

Heretofore, cotton, pulp, paper, sponge, etc. have been used as absorptive materials. A hydrolyzate of a starch/acrylonitrile copolymer crosslinked polysodium acrylate, crosslinked carboxymethylcellulose, a hydrolyzate of an acrylate ester/vinyl acetate copolymer have been proposed as high-molecular absorptive materials in recent years.

These absorptive materials, as such or in the form of a composite material, have been used as sanitary napkin, disposable diaper, human absorption pad for medical use, agricultural water retaining material and dewfall inhibitor. High-molecular materials have been extensively used in the field of mainly sanitary materials in recent years, since paper, pulp, etc. have disadvantages in that they are bulky and have low absorption.

However, even when these absorptive materials are used as the sanitary materials, the absorbed liquid oozes therefrom under load so that they become sticky and foul. When they are used as a soil conditioner, a water absorption/water discharge cycle is so short that they can not exhibit satisfactory water retentivity over a long period of time. Therefore, a satisfactory high-molecular absorptive material suitable for use as a sanitary material has not been found yet.

The inventors of the present invention already proposed a water-absorptive material excellent in water absorption performances (Japanese Patent Publication No. 30710/1979) and also proposed an improved water-absorptive material (Japanese Patent Laid-Open No. 158210/1982). However, these water-absorptive materials also have a problem that, although they have excellent gel strength upon absorption of water, they show markedly low preformance with respect to salt resistance because it is a polyelectrolyte, so that it has been demanded that a water-absorptive material excellent in salt resistance as well as in water absorption rate and gel strength is developed as early as possible.

The invention to overcome the above discussed problems is an absorptive material which comprises a high-molecular absorptive material containing carboxyl or carboxylate groups and having physical properties such that a physiological saline absorption quantity (hereinafter referred to simply as absorption quantity) is 40 to 90 grams per one gram of the polymer, preferably from 45 to 75 grams, a physiological saline absorption rate) is at least 8 ml per 0.3 gram of the polymer, preferably from 8 to 13 ml, and a gel strength after swelling by saturation with ion-exchange water (hereinafter referred to as swollen gel strength) is 33 to 200 g/cm², preferably from 35 to 100 g/cm².

Generally, performances required for high-molecular absorptive materials include absorption quantity, absorption rate and gel strength, and it is desirable that they are excellent in all the performances. Particularly, it is desirable that sanitary materials such as sanitary napkin or disposable diaper are excellent in absorption capacity and absorption rate and little causes oozing of the absorbed liquid therefrom under pressure.

Accordingly, both require the same performances. The absorption rate of the high-molecular absorptive material plays a role in that leakage can be avoided by rapidly absorbing a liquid such as menstrual blood or urine and, in addition, a feeling of dryness can be imparted to the surface (the side in contact with the skin) of a sanitary material. The gel strength plays a role in surely retaining the liquid. If the gel strength is low, the high-molecular material is broken by a load such as body weight and exposed to the surface of the sanitary material, thus giving unpleasant feeling.

An important aspect of the present invention resides in that the high-molecular material having the aforementioned absorption physical properties is a water-insoluble high-molecular material containing carboxyl or carboxylate groups and having a crosslinking density gradient.

Usually, there is the following correlation among the absorption physical properties (absorption quantity, absorption rate and gel strength) of the high-molecular material.

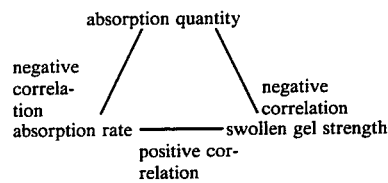

No high-molecular absorptive material satisfying all such physical properties as an absorptive quantity of 40 to 90 g/g-polymer, an absorption rate of at least 8/0.3 g-polymer and a swollen gel strength of 33 to 200 g/cm² is currently commercially available.

The high-molecular absorptive material satisfying all the physical properties will be one in which there is a difference in a crosslinking density between the inside and the surface of the particle and the crosslinking density in the surface thereof is higher than that in the inside thereof. .

Examples of the backbones of such high-molecular absorptive materials having crosslinking density gradient include a starch/acrylic acid (or salt) graft copolymer, polyacrylic acid (or salt) and a hydrolyzate of an acrylate ester/vinyl acetate copolymer, among which polyacrylic acid and polyacrylate salt are preferred. Other monomers such as methacrylic acid, a (meth)acrylate ester and (meth)acrylamide may be used as comonomers copolymerizable with the polyacrylate salt in a quantity which does not cause lowering in the absorption physical properties. Methods of imparting a crosslinking density gradient to the high-molecular absorptive material include:

1. a method wherein a hydrophilic crosslinked polymer having hydroxyl and/or carboxyl groups (or carboxylate groups) is dispersed in a solvent mixture of water and a hydrophilic organic solvent (in a mixing ratio of water to solvent of 50~5 to 50~95) and catalytically reacted with a crosslinking agent capable of reacting with the functional groups of said hydrophilic crosslinked polymer to further crosslink the surface thereof (after the completion of the polymerization, the polymer may be dispersed in the solvent mixture without recovering the polymer to carry out the crosslinking reaction); and 2. a method wherein an aqueous solution of a hydrophilic monomer having a carboxyl group (or a carboxylate group) containing a water-soluble polymerization initiator is dispersed and suspended in a hydrophobic solvent in the presence of a protective colloid to carry out a polymerization reaction, the water content of the resulting hydrophilic polymer is controlled to 10 to 40 wt. % and the polymer is catalytically reacted with a crosslinking agent reactive with the functional group of the polymer to further crosslink the surface thereof.

The method (2) is preferred from the viewpoints of the polymerization reaction and the crosslinking reaction.

The invention provides a process for producing a highly water-absorptive polymer by suspending an aqueous solution of carboxyl group-containing water-soluble ethylenically unsaturated monomer containing no crosslinking agent by dispersing it in a hydrocarbon or a halogenated aromatic hydrocarbon and polymerizing the resulting suspension, which is characterized in that a cellulose ester or a cellulose ether which is oil-soluble at the polymerization temperature is used as a protective colloid to increase the particle size of the obtained polymer to 100 μm or above and the moist, carboxyl group-(or carboxylate group)-containing, hydrophilic polymer having a moisture content controlled in the range of 10 to 40 wt. % (based on the polymer) is crosslinked with a crosslinking agent having at least two functional groups reactive with the carboxyl groups or carboxylate groups. A reference to a moisture content may be replaced by another reference to a water content.

Examples of the carboxyl group-containing, water-soluble ethylenically unsaturated monomers generally include acrylic acid, a salt thereof, methacrylic acid and a salt thereof. Further the monomer may be used with another monomer, co-monomer, such as maleic acid, itaconic acid, acrylamide, 2-acrylamido-2-methylpropanesulfonic acid, 2-(meth)acryloylethanesulfonic acid, or 2-hydroxylethyl (meth)acrylate, in an amount within a range not to lower the performance of a water-absorptive polymer.

It is added that an alkali metal salt of a monomer and an alkali metal salt of a produced polymer according to the invention include both a partial salt and the complete salt thereof.

The cellulose esters or cellulose ethers which are oil-soluble at a polymerization temperature used as a protective colloid in the W/O suspension polymerization in the present invention are those which are insoluble or difficultly soluble at room temperature in a hydrocarbon or a halogenated aromatic hydrocarbon as a dispersion medium and are soluble therein at a polymerization temperature (50° C. or above).

Examples of the cellulose esters or ethers include cellulose acetate, cellulose propionate, cellulose butyrate, cellulose acetate propionate, cellulose acetate butyrate, cellulose acetate phthalate, ethylcellulose, benzylcellulose, and ethylhydroxyethylcellulose, among which cellulose acetate butyrate, ethylcellulose and ethylhydroxyethylcellulose are preferable.

Preferable dispersion media used in the present invention include hydrocarbons and halogenated aromatic hydrocarbons having 6 to 10 carbon atoms. Examples of these hydrocarbons include aromatic hydrocarbons such as benzene, ethylbenzene, toluene and xylene, alicyclic hydrocarbons such as cyclohexane, methylcyclohexane, cyclooctane and decalin, aliphatic hydrocarbons such as hexane, pentane, heptane, and octane, and halogenated hydrocarbons such as chlorobenzene, bromobenzene, and dichlorobenzene, among which toluene, xylene, cyclohexane, methylcyclohexane, hexane, heptane, chlorobenzene, and dichlorobenzene are preferable. The use of a mixture of at least two of these solvents as the dispersion medium is also possible, depending upon the kind of the cellulose ester or ether used. Even a single solvent can be used as the dispersion medium by suitably selecting a cellulose or ether used. The use of a single solvent facilitates the recycling of a dispersion medium and is extremely advantageous in industry.

Cellulose derivatives which are suitable when toluene, xylene, ethylbenzene, chlorobenzene, dichlorobenzene, or the like is used alone as the dispersion medium are ethylcellulose of an ethoxy group content of 43 to 47 wt. % and cellulose acetate butyrate of a butyryl group content of 20 to 50 wt. %. A cellulose derivative which is suitable when cyclohexane, cyclopentane, methylcyclohexane, decalin or the like is used alone as the dispersion medium is ethylcellulose of an ethoxy group content of 47 to 50 wt. %. A cellulose derivative which is suitable when n-hexane, n-heptane, n-octane, or the like is used alone as the dispersion medium is ethylhydroxyethylcellulose. The amount of the protective colloid used falls within the range of 0.05 to 10 wt. %, preferably 0.5 to 5 wt. %, based on the dispersion medium. The polymerization can be carried out at a polymerization temperature falling within the range from 50° C. to the boiling point of the dispersion medium. This temperature is preferably 60° C. or above, and it is preferred from the viewpoint of removal of the heat of polymerization that the polymerization is carried out at the azeotropic temperature of a mixture of a dispersion medium and water. Although the ratio of the dispersion medium to an aqueous monomer solution can be varied widely, it is suitably within the range of, usually, 1:1 to 5:1 from the view of removal of the heat of polymerization and control of the polymerization temperature.

It is an essential point for achieving the object of the present invention that a moist, carboxyl group- or carboxylate group-containing, hydrophilic polymer having an extremely large particle diameter, obtained by a W/O suspension polymerization process wherein an oil-soluble cellulose ester or a cellulose ether is used as a dispersing agent, be crosslinked when it has a moisture content within a specified range.

In addition, the W/O suspension polymerization process is desirable because the control of the water content of the wetted, or moist, polymer is an essential requisite in the present invention and a dehydration step is usually necessary after the production of a polymer. In producing the carboxyl group (or carboxalate group)-containing hydrophilic polymer, a crosslinking agent may be added without detriment to the effect of the present invention so long as it is added in an extremely small amount. It is desirable from the viewpoint of gel strength upon absorption of water that the polymer is selfcrosslinked.

A particularly important factor in this invention is the moisture content of the moist hydrophilic polymer when a crosslinking reaction is conducted with a crosslinking agent. Heretofore, processes for producing a water-absorptive polymer, wherein a crosslinking reaction is effected after polymerization, are well-known.

For example, Japanese Patent Laid-Open No. 131608/1981 describes a process in which a polyacrylate salt is crosslinked in a solvent mixture of water and a hydrophilic organic solvent, and Japanese Patent Publication No. 28505/1982 describes a process in which polyacrylic acid (or its salt) is crosslinked in the presence of water.

Since, however, the moisture content of each of these moist polymers is 50 wt. % or above and especially that of the latter is 70 wt. % or above, the effect of the present invention can not be realized at such a high moisture content.

Usually, a hydrophilic polymer can be obtained by polymerizing a monomer at a concentration of 45 wt. % or below, i.e., at a moisture content of 55 wt. % or above. In practicing the present invention, therefore it is necessary to control the moisture content of a moist hydrophilic polymer product obtained by a common process.

According to the present invention, it is an essential requisite that the moisture content falls within the range of 10 to 40 wt. %, based on the moist hydrophilic polymer. More desirably, it is 15 to 35 wt. % based on the total weight. When the moisture content of the moist hydrophilic polymer is outside the above range, the produced water-absorptive polymer is deficient in water absorption quantity and/or water absorption rate and gel strength, so that the marked effect of the present invention can not be obtained. The desired effect can be attained in the present invention by controlling the moisture content of a moist polyacrylic acid polymer obtained by a W/O suspension polymerization process wherein an oil-soluble cellulose ester or a cellulose ether is used as a dispersing agent within the above range by concentration.

The crosslinking agents which can be used in the present invention include any of compounds that have at least two functional groups reactive with carboxyl groups (or carboxylate groups). They include, for example, polyglycidyl ethers such as ethylene glycol diglycidyl ether, polyethylene glycol diglycidyl ether, and glycerin triglycidyl ether, haloepoxy-compounds such as epichlorohydrin and α-methylchlorohydrin, polyaldehydes such as glutaradehyde and glyoxal, polyols such as glycerin, pentaerythritol and ethylene glycol, and polyamines such as ethylenediamine. Preferably, it is a polyglycidyl ether such as ethylene glycol diglycidyl ether.

Although the amount of the crosslinking agent may vary with its kind and the kind of a polymer, it is usually within the range of 0.01 to 5.0 wt. % based on the polymer. When the amount of the crosslinking agent is smaller than 0.01 wt. %, the effect of addition is not sufficient, while when it exceeds 5.0 wt. %, the crosslinking density increases, which results in a low water absorption quantity. This is undesirable in the present invention.

The polymer produced according to the present invention has an extremely large particle diameter, so that no countermeasures is necessary against dusting. In addition, because of its large particle diameter, the polymer is endowed with a high water absorptivity and a high water absorption rate. It is possible to obtain a polymer having high salt resistance, water absorption rate and gel strength upon absorption of water by controlling the moisture content of the obtained moist hydrophilic polymer and crosslinking it. The highly water-absorptive polymer can be produced only when the oil-soluble cellulose ester or cellulose ether as mentioned above is used as a protective colloid and a W/O suspension polymerization process which can allow easy moisture control is adopted.

It is possible to obtain a water-absorptive material excellent in salt resistance, water absorption rate and gel strength upon absorption of water by the process of the present invention, and the obtained material can be used highly advantageously as an agricultural water-retaining agent or a water-absorbing agent for sanitary materials. The highly water-absorptive polymer obtained by the process of the present invention can be used, especially, in the field of paper diapers which can quickly absorb a large quantity of urine and is not broken even when wetted with urine, or the field of sanitary napkins which can absorb blood and must hold it tightly even under pressure. Thus, "leakage" and "discomfort" can be eliminated.

The process as shown above may provide a polymer having such physical properties as defined before. By controlling the polymerization conditions, the absorption quantity can be increased to a value of as surprisingly high as 100 g or above per gram of polymer, but there is the aforementioned correlation between the absorption physical properties and the absorption rate and the gel strength are greatly lowered so that such a high absorption quantity is not preferred. For example, when a high-molecular absorptive material having a gel strength lower than 33 g/cm$^2$ is applied to a disposable diaper, such a material is broken by the baby weight. When the absorption rate is lower than 8 ml/0.3 g-polymer, the quantity of the high-molecular material to be used must be increased. Otherwise leakage will occur unfavorably. When these facts are taken into consideration, particularly preferred physical properties of the high-molecular absorptive material are such that the absorption quantity is 40 to 90 g/g-polymer, the absorption rate is at least 8 ml/0.3 g-polymer and the gel strength is 33 to 200 g/cm$^2$.

The polymer absorbent according to the invention may be in the form of flakes, spherical particles, porous particles or botryoidal chains.

Further the invention provides various applications of the above mentioned absorbent polymer. The polymer as obtained in the invention process is useful as an absorbent and therefore effectively used in a sanitary article such as a sanitary napkin and a disposable diaper. Preferable embodiments of a sanitary article according to the invention are illustrated below.

A sanitary napkin comprises a liquid-permeable surface material to be in contact with the skin, a liquid-impermeable leakproof material and an absorption layer interposed between said two materials, characterized in that the absorption layer comprises a high molecular absorbent and a cotton-like pulp and/or absorbent paper which absorbent has a physiological saline absorption quantity of 40 to 90 g/g-polymer, a physiological saline absorption rate of at least 8 ml/0.3 g-polymer and a gel strength after swelling by saturation with ion-exchanged water of 33 to 200 g/cm$^2$.

A disposable diaper comprises a liquid-permeable surface sheet, a liquid-impermeable back sheet and an absorption layer placed between said two sheets, characterized in that the absorption layer comprises a high molecular absorbent and a cotton-like pulp and/or paper which absorbent has a physiological saline absorption quantity of 40 to 90 g/g-polymer, a physiological saline absorption rate of at least 8 ml/0.3 g-polymer and a gel strength after swelling by saturation with ion-exchanged water of 33 to 200 g/cm².

A disposable diaper comprises a liquid-permeable surface sheet, a liquid-impermeable back sheet and an absorption layer placed between said two sheets, characterized in that the absorption layer comprises a high molecular absorbent and a cotton-like pulp and/or paper which absrobent has a physiological saline absorption quantity of 40 to 90 g/g-polymer and a physiological saline absorption rate of at least 8 ml/0.3 g-polymer and which absorbent retains its form of swollen gel for at least 8 h after absorption of urine.

Since the polymer absorbent according to the invention is unexpectedly improved in respect to the above shown properties, it serves to absorb and keep liquid in a sanitary article more effectively than fluff pulp and another absorbent paper. Accordingly such a sanitary article is designed so as to mainly comprises the polymer in the absorption layer.

It is an important requisite in the present invention that the high molecular absorbent which is a main component of the absorption layer has all of high absorption quantity, absorption rate and gel strength, particularly the high absorption rate and form retentivity in a swollen state.

The absorption rate of the high molecular absorbent is an important factor in the production of the disposable diapers, since it realizes a merit of keeping urine from leakage and also a feeling of dryness on the diaper surface (the surface to be in contact with the skin). Another important factor in the production of the disposable diapers is the gel strength of the high molecular absorbent, since when the form of the swollen absorbent cannot be retained for a long time after the absorption of urine, the absorbent is disintegrated by the weight of the user and exposed to the diaper surface to make the user unpleasant. Thus, the disposable diapers which do not realize the unpleasant feeling cannot be produced unless a high molecular absorbent having all of high absorption quantity and absorption rate and excellent form retentivity of the swollen gel is used.

The present invention will now be described in detail with reference to Examples and Comparative Examples, but it should be understood that the present invention is not limited to these examples.

The acetyl group content, butyryl group content and ethoxy group content of cellulose esters or ethers used herein are as follows:
  cellulose acetate butyrate (a product of Eastman Kodak, trademark CAB 381-20): acetyl group content of 13%, butyryl group content of 37 wt. %,
  ethylcellulose (a product of Hercules, trademark Ethylcellulose N-200): ethoxy group content of 47.5 to 49.0 wt. %.

Figure 1:
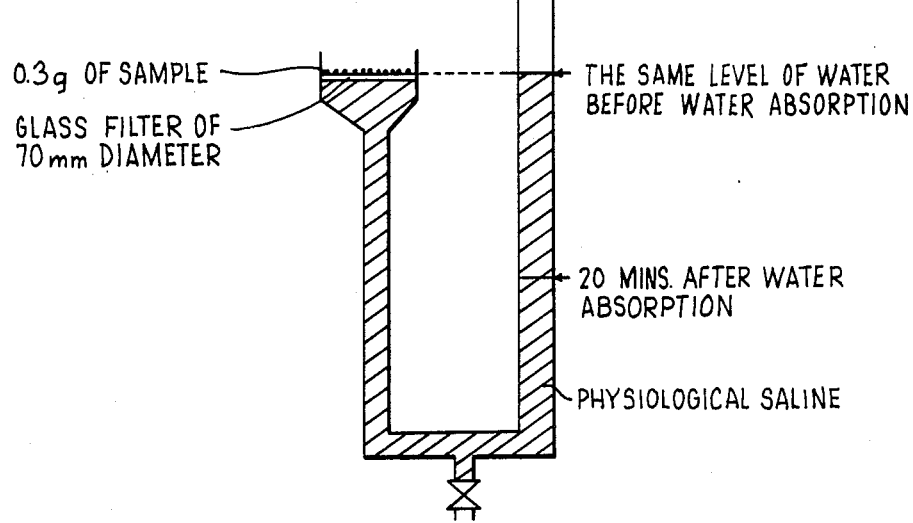
FIGS. 1 and 2 are each a schematic diagram of an apparatus used in the measurement of the physical property of a highly water-absorptive polymer of the present invention.
Figure 2:
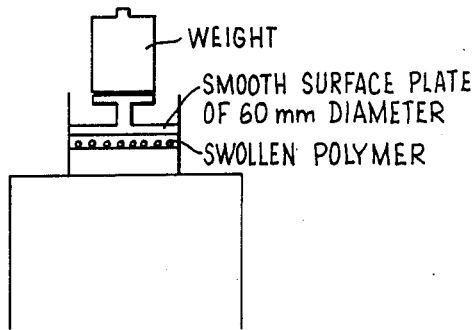

The water absorption quantities, water absorption rates and gel strengths in Examples and Comparative Examples are values determined by the following procedures. Namely, about 1 g of a polymer is dispersed in a large excess of ion-exchanged water or 0.9% physiological saline, allowed to swell fully, and filtered through an 80-mesh metal gauge according to JIS, Japanese Industrial Standard. The obtained swollen polymer is weighed, and this weight (W) is divided by the initial weight ($W_0$) of the polymer. Namely, the water absorption quantity (g/g) is represented by $W/W_0$. The water absorption rate is measured by using an apparatus as shown in FIG. 1. 0.3 g of a polymer is sprayed over a glass filter of 70 mm diameter while the water levels of physiological saline is kept the same and the water absorption rate is expressed in terms of the quantity of the physiological saline absorbed for 20 minutes. The gel strength upon absorption of water is determined by using an apparatus as shown in FIG. 2. A polymer fully swollen with ion-exchanged water and filtered through an 80-mesh metal gauge is sandwiched between 60 mm diameter plates having a smooth surface. Then a weight is applied and the minimum weight ($W_1$) at which the swollen polymer particles are broken is measured. The gel strength upon absorption of water is defined as the weight ($W_1$) divided by the area. Namely, gel strength is $(W_1)/3 \times 3 \times 3.14 = W_1/28.26$.

EXAMPLES 1 THROUGH 3

A 500-ml four-necked, round-bottomed flask fitted with a stirrer, reflux condenser, dropping funnel, and nitrogen gas inlet tube was charged with 230 ml of cyclohexane and 1.68 g of Ethylcellulose N-200, and the mixture was heated to 75° C. Separately, 30 g of acrylic acid was neutralized in an Erlenmeyer flask with a solution of sodium hydroxide (13.4 g) in water (39 g). The monomer concentration of the aqueous monomer solution was 45% (water content of 55%). 0.1 g of potassium permanganate was dissolved in this solution. This solution was polymerized by adding it dropwise to the above four-necked flask in a nitrogen atmosphere over 1.5 hours and the reaction mixture was kept at 70° to 75° C. for 0.5 hour to complete the polymerization. The moisture content of the polymer suspended in the cyclohexane was controlled by azeotropic distillation of water (the cyclohexane was refluxed) to 35%, 27%, or 20%. A solution of ethylene glycol diglycidyl ether (0.03 g) in water (1 ml) was added to each polymer at 73° C. Each mixture was kept at this temperature for 2 hours. The cyclohexane was removed, and the polymers were dried in vacuum at 80° to 100° C. to obtain water-soluble polymers of a median diameter of 100 to 350 μm.

EXAMPLE 4

The polymerization in this example was carried out in the same manner as in Example 1 except that the Ethylcellulose N-200 was replaced with 2.12 g of ethylhydroxyethylcellulose, that the cyclohexane was replaced with 230 ml of n-hexane, and that the reaction mixture was heated to 65° C. After the polymerization, the moisture content of the moist polymer was controlled to 22% by azeotropic distillation of water and a solution of glycerin diglycidyl ether (0.04 g) in water (1 ml) was added thereto at 70° C. The mixture was kept at this temperature for 3 hours and the n-hexane was removed. The formed polymer was dried in vacuum at 80° to 100° C. to obtain a water-absorptive polymer of a median particle diameter of 100 to 350 μm.

EXAMPLE 5

The polymerization in this example was carried out in the same manner as in Example 1, except that the monomer concentration of the aqueous monomer solution was 35% and that 0.003 g of N,N'-methylenebisacrylamide was used additionally. After the polymerization, the moisture content of the moist polymer was controlled to 27% by azeotropic distillation of water and a solution of polyethylene glycol diglycidyl ether (n=9) (0.15 g) in water (1 ml) was added thereto at 60° C. The mixture was kept at this temperature for 3 hours and the cyclohexane was removed. The formed polymer was dried in vacuum at 80° to 110° C. to obtain a water-absorptive polymer of a median particle diameter of 100 to 350 μm.

EXAMPLE 6

The polymerization reactor used in Example 1 was charged with 230 ml of monochlorobenzene and 2.3 g of cellulose acetate butyrate, and the mixture was heated to 80° C. Separately, 26 g of acrylic acid and 4 g of acrylamide were neutralized in a flask with a solution of 98% sodium hydroxide (11.0 g) in 44 g of ion-exchanged water. 0.1 g of ammonium persulfate was added thereto and dissolved to form an aqueous monomer solution. The monomer concentration of the water phase was about 46 wt. %. After the polymerization, the moisture content of the polymer was controlled to 25% by azeotropic distillation of water and the resulting polymer was treated in the same way as in Example 1 to obtain a water-absorptive polymer of a median particle diameter of 100 to 250 μm.

Comparative Example 1

The polymerization procedure of Example 1 was repeated except that 0.03 g of ethylene glycol diglycidyl ether was added to the aqueous monomer solution and that the crosslinking reaction was carried out simultaneously with the polymerization reaction. After the completion of the polymerization, cyclohexane was removed and the polymer was dried at a temperature of 80° to 100° C. under vacuum to afford a water-absorptive polymer having a median particle size of 100 to 350 μm.

Comparative Example 2

The polymerization procedure of Example 1 was repeated. After the completion of the polymerization, an aqueous solution of 0.03 g of ethylene glycol diglycidyl ether in 1 ml of water was added (the water content of the hydrated polymer being 55%) and the mixture was kept at 73° C. for one hr. After the completion of the crosslinking reaction, cyclohexane was removed and the polymer was dried at a temperature of 80° to 100° C. under vacuum to afford a water-absorptive polymer having a median particle size of 100 to 350 μm.

Comparative Example 3

The polymerization procedure of Example 1 was repeated. Thereafter, cyclohexane was removed and the polymer was dried at a temperature of 70° to 80° C. under vacuum. The water content of the resulting polymer was 7%. The polymer was re-dispersed and re-suspended in cyclohexane and an aqueous solution of 0.03 g of ethylene glycol diglycidyl ether in 1 ml of water was added thereto. The mixture was kept at 70° C. for one hr. Cyclohexane was removed and the polymer was dried at a temperature of 80° to 100° C. under vacuum to afford a water-absorptive polymer.

Comparative Example 4

The polymerization procedure of Example 1 was repeated except that 0.005 g of potassium persulfate was used. The resulting polymer had a median particle size of 100 to 350 μm.

Comparative Example 5

Commercially available crosslinked polysodium acrylate marketed under trade name of Aquakeep 10SH.

Comparative Example 6

Commercially available crosslinked starch/acrylic acid graft copolymer marketed under trade name of Sanwet IM-1000.

Comparative Example 7

The polymerization in this comparative example was carried out in the same manner as in Example 1, except that a solution of ethylene glycol diglycidyl ether (0.03 g) in water (1 ml) was added when the moisture content of the moist polymer was controlled to 45% by azeotropic distillation of water and that the mixture was kept at 60° C. for 2 hours. After the crosslinking reaction, the cyclohexane was removed and the polymer was dried in vacuum at 80° to 100° C. to obtain a water-absorptive polymer of a median particle diameter of 100 to 350 μm.

Comparative Examples 8 and 9

The polymerization in these comparative examples was carried out in the same manner as in Example 1, except that the cyclohexane was replaced with 230 ml of n-hexane, that the Ethylcellulose N-200 was replaced with 1.8 g of sorbitan monostearate, and that the mixture was heated to 65° C. After the polymerization, the moisture content of the polymer was controlled to 27% or 20% by azeotropic distillation of water and the resulting polymer was treated in the same manner as in Example 1 to obtain water-absorptive polymers of a median particle diameter of 10 to 70 μm.

Then each product of the above shown examples and comparative examples were examined in a sanitary article. Results are shown in Table 1.

Sanitary Napkin 2.2 g of a cotton-like pulp was halved roughly to form upper and lower layers. 0.3 g of one of the high molecular absorbents was spread between the two layers and they were compressed to form an absorption layer. 10 g of equine blood was absorbed in the center of the obtained absorption layer (70 mm × 150 mm). After 3 min, the blood spueezed out under a pressure of 30 g/cm² in 2 min was absorbed by a 100 cm² filter paper and the quantity thereof was measured. Thereafter the form of the swollen high molecular absorbent was observed macroscopically to confirm the form retention.

Sanitary Diaper (1)

10 g of a cotton-like pulp was halved roughly to form upper and lower layers, 2.5 g of one of the high molecular absorbents was spread between the two layers snd they were compressed to form an absorption layer. 30 ml of an artificial urine was absorbed in the center of the obtained absorption layer (120 mm × 200 mm). After 15 min, the liquid squeezed out under a pressure of 35 g/cm² in 2 min was absorbed by a 100 cm² filter paper and the quantity thereof was measured. Then the swollen polymer was observed to examine a shape thereof.

Sanitary Diaper (2)

25 g of a cotton-like pulp was halved roughly to form upper and lower layers. 5 g of one of the high molecular absorbents was spread between the two layers and they were compressed to form an absorption layer. The thus obtained absorption layer (130 mm × 300 mm) was combined with a surface sheet and a back sheet to form a disposable diaper. 100 ml of urine of a 6-month male baby was poured thereon and a change of the state of a gel of the high molecular absorbent with time was observed macroscopically.

In the results of the form of the absorbent in the napkin, the mark "o" shows "form unchanged" and the mark "x" indicates that the absorbent has been disintegrated. In the results of the state of gel the marks "o" and "x" show:

TABLE 1

| No. | Water absorption quantity (g/g) | | Water absorption rate (ml/0.3 g, 20 min) | Gel strength (g/cm$^2$) | Quantity of squeezed liquid (g) in the napkin | Form of the absorbent in the napkin | Quantity of squeezed liquids (g) in the diaper | State of gel | | | |
|---|---|---|---|---|---|---|---|---|---|---|---|
| | Ion-exchanged water | Physiological saline | | | | | | 8h | 10h | 12h | 14h |
| Example | | | | | | | | | | | |
| 1 | 510 | 72 | 11.4 | 40.6 | 0.8 | o | 2.2 | o | o | o | o |
| 2 | 600 | 73 | 11.5 | 41.3 | 0.7 | o | 2.0 | o | o | o | o |
| 3 | 750 | 85 | 12.3 | 35.2 | 0.4 | o | 1.5 | | | | |
| 4 | 605 | 78 | 11.8 | 42.3 | 0.5 | o | 1.8 | | | | |
| 5 | 530 | 73 | 11.2 | 43.5 | 0.8 | o | 2.4 | | | | |
| 6 | 525 | 73 | 10.9 | 42.7 | | | | | | | |
| Comparative Example | | | | | | | | | | | |
| 1 | 400 | 50 | 7.5 | >268.6 | 3.0 | o | 5.0 | | | | |
| 2 | 410 | 49 | 7.5 | 252.7 | 3.0 | o | 5.2 | | | | |
| 3 | 550 | 60 | 7.7 | 53.8 | 3.5 | o | 6.0 | | | | |
| 4 | | 106 | 5.8 | 21.6 | 4.6 | x | 5.5 | | | | |
| 5 | | 78 | 11.8 | 29.8 | 0.7 | x | 2.0 | x | x | x | |
| 6 | | 67 | 5.2 | 25.9 | 5.2 | x | 6.2 | | | | |
| 7 | 435 | 51 | 7.8 | 104.2 | | | | | | | |
| 8 | 585 | 74 | 10.2 | 15.8 | | | | | | | |
| 9 | 690 | 79 | 10.5 | 18.2 | | | | | | | |

Table 1 clearly shows that the polymers obtained according to the present invention have excellent absorption performances, i.e., excellent salt resistance, water absorption rate and gel strength.

The embodiments of the invention in which an exclusive property or privilege is claimed are defined as follows:

1. A process for preparing a water-insoluble, water-swellable polymer, which comprises the steps of:
dispersing (1) an aqueous solution of a water-soluble, ethylenically unsaturated monomer having a carboxyl or carboxylate group in the molecule, in (2) a hydrophobic organic liquid dispersion medium to form a water-in-oil suspension, said suspension also containing a protective colloid selected from the group consisting of cellulose esters and cellulose ethers, said protective colloid being insoluble or sparingly soluble in said dispersion medium at room temperature;
then polymerizing said monomer under water-in-oil suspension polymerization conditions, in the presence of a water-soluble radical polymerization initiator, at an elevated polymerization temperature, said protective colloid being soluble in said dispersion medium at said elevated polymerization temperature, whereby to form particles of a hydrophilic polymer dispersed in said liquid dispersion medium;
then removing water from said dispersion so that said hydrophilic polymer has a water content of from 10 to 40 percent by weight,
then mixing said dispersion in which said hydrophilic polymer has a water content of from 10 to 40 percent by weight, with a crosslinking agent containing at least 2 functional groups reactive with carboxyl and carboxylate groups, under conditions effective to crosslink said polymer and to provide a higher crosslinking density on the surfaces of said polymer particles than in the interiors of said polymer particles; and
then removing said dispersion medium to obtain said polymer particles.

2. A process for preparing a water-insoluble, water-swellable polymer, which comprises the steps of:
dispersing (1) an aqueous solution of water-soluble, ethylenically unsaturated monomer having a carboxyl or carboxylate group in the molecule, said aqueous solution containing no crosslinking agent, in (2) a hydrophobic, hydrocarbon or halogenated aromatic hydrocarbon, liquid dispersion medium so that the ratio of said dispersion medium to said aqueous solution is from 1/1 to 5/1, whereby to form a water-in-oil suspension, said suspension also containing from 0.05 to 10 wt.%, based on said dispersion medium, of a protective colloid selected from the group consisting of cellulose esters and cellulose ethers, said protective colloid being insoluble or sparingly soluble in said dispersion medium at room temperature;
then polymerizing said monomer under water-in-oil suspension polymerization conditions, in the presence of a water-soluble radical polymerization initiator, at an elevated polymerization temperature of from 50° C. up to the boiling point of the dispersion medium, said protective colloid being soluble in said dispersion medium at said elevated polymerization temperature, whereby to form particles of a hydrophilic polymer dispersed in said liquid dispersion medium, said particles having a particle size of at least 100 micrometers;
then removing water from said dispersion so that said hydrophilic polymer has a water content of from 10 to 40 percent by weight, then mixing said dispersion in which the hydrophilic polymer has a water content of from 10 to 40 percent by weight, with from 0.01 to 5 wt.%, based on said polymer, of a crosslinking agent containing at least 2 functional groups reactive with carboxyl and carboxylate groups, under conditions effective to crosslink said polymer and to provide a higher crosslinking density on the surfaces of said polymer particles than in the interiors of said polymer particles; and then removing said dispersion medium to obtain said polymer particles.

3. A process as claimed in claim 2 in which in said removing step, water is removed from said dispersion until said hydrophilic polymer has a water content of 15 to 35%.

4. A process as claimed in claim 2 in which said monomer is acrylic acid, a salt of acrylic acid, methacrylic acid or a salt of methacrylic acid.

5. A process as claimed in claim 2 in which said monomer comprises sodium acrylate.

* * * * *